United States Patent [19]

Lee

[11] 4,085,747
[45] Apr. 25, 1978

[54] INFUSION PUMPS AND DOSAGE CONTROL MEANS THEREFOR

[75] Inventor: Arnold St. Jacques Lee, Red Bank, N.J.

[73] Assignee: Milstein Medical Research Foundation, Inc., New York, N.Y.

[21] Appl. No.: 750,189

[22] Filed: Dec. 13, 1976

[51] Int. Cl.² .............................................. A61M 5/00
[52] U.S. Cl. .............................. 128/214 F; 128/218 A; 128/DIG. 12
[58] Field of Search ................... 128/234, 213, 214 R, 128/214 F, 218 R, 218 A, 218 P, 218 PA, 218 C, DIG. 1, DIG. 12, 215

[56] References Cited

U.S. PATENT DOCUMENTS

| | | | |
|---|---|---|---|
| 2,457,977 | 1/1949 | Cookson | 128/218 A |
| 2,491,978 | 12/1949 | Helfman et al. | 128/218 R |
| 2,498,672 | 2/1950 | Glass | 128/218 A |
| 3,362,406 | 1/1968 | Logsdon | 128/218 R |
| 3,964,139 | 6/1976 | Kleinmann et al. | 128/214 F X |

Primary Examiner—John D. Yasko

[57] ABSTRACT

An infusion pump suitable, e.g., for delivering an adjustable, metered amount of a drug to a patient includes a pre-sterilized, thin-walled plastic syringe which is employed solely as a sterile inner liner for an outer, thick-walled split cylindrical clamp that is axially coextensive with the plastic syringe barrel. The required effect is obtained by inwardly squeezing the clamp against the wall of the plastic syringe until the two parts of the clamp come together to define a bore of a standard inner diameter. A plunger, which is tightly engaged with the wall of the so-deformed plastic syringe to prevent leakage of the drug, is normally driven at one of a plurality of selectable speeds by means of a gear box that is specially constructed to vary the plunger speed travel, and thereby the fluid flow rate of the drug in the syringe, in successive steps with each step being a predetermined constant fraction of the next-preceeding step. Facilities are also provided for introducing a one-shot increase in dosage into the so-selected fluid flow rate without interrupting such flow rate.

18 Claims, 6 Drawing Figures

INFUSION PUMPS AND DOSAGE CONTROL MEANS THEREFOR

BACKGROUND OF THE INVENTION

The invention relates to infusion pumps suitable, e.g., for continuously delivering a drug to a patient at a rate determined by one of a plurality of predetermined speeds of movement of a plunger in the pump syringe barrel. The invention also relates to discretely adjustable speed conversion means which may be employed, e.g., for the selection of one of the plunger speeds of an infusion pump, and thereby the rate of metering of the drug to a patient.

Conventional types of infusion pumps employ a syringe barrel with a movable plunger for administering a constant flow of a drug to a patient, with the position of the plunger being adjusted by a mechanized dose rate control that is powered by a prime mover, typically a variable-speed motor. In general, the dose rate control may comprise a gear box or other suitable speed conversion means for reducing the speed of the variable-speed motor to one of a plurality of relatively slow settings appropriate for driving the plunger in the syringe barrel.

The syringe barrel of conventional infusion pumps is made out of either glass or plastic. The glass device is extremely accurate in its dimensions, and thereby in the accuracy of the setting of the dose rate; however, it is necessary to thoroughly wash and sterilize such glass syringes after each use. Any residual contaminants, even though sterile, can be fatal when the glass syringe is re-used for another patient.

While such dangers may be eliminated by using a standard, "throw-away" pre-sterilized syringe, other problems crop up in their place. For example, such pre-sterilized syringes are generally manufactured under poor quality control, so that their interior dimensions are not accurate. Such inaccuracies, in turn, lead both to irregularities in the dose rate setting and to poor fit of the plunger inside the barrel. Under the latter condition, and particularly during the very slow rates of flow of the drug which are ordinarily required, the medication may escape from the barrel via the gap between the plunger and the barrel, rather than being infused into the patient as desired.

An additional disadvantage of such existing infusion pumps is their relatively coarse control of the setting of dose rate. For example, where the rate controller is a mechanized gear box whose rate may be set by a suitable rate control knob, it is not uncommon to observe a 50 – 100% change in dose rate between a pair of adjacent settings of the rate control knob. Moreover, when, as is conventional, the rate controlling gear boxes are driven by servo-controlled variable-speed electric motors, unpredictable changes in line voltage and the like may result in dangerous and sometimes fatal changes in the ultimate dose rate from the pump.

SUMMARY OF THE INVENTION

Such disadvantages are overcome with the arrangement of the present invention. In an illustrative embodiment, the plunger-receiving barrel of the infusion pump is in the form of a standard pre-sterilized syringe which is positionable coaxially within a split cylindrical clamping member that is axially coextensive with the syringe. The inner diameter of the clamping member is adjustable inwardly to an inner limit representing a fixed standard inner diameter slightly smaller than the nominal outer diameter of the pre-sterilized syringe. As a result, when the clamping member is adjusted inwardly over the syringe, the wall of the syringe is deformed into conformance with the standard inner diameter of the clamping member, so that the syringe forms an intimately adhering liner for the clamping member. In effect, the dimensional accuracy of the normally inaccurate "throw-away" syringe is increased by this technique to that of a glass syringe, without sacrificing the necessary sterility of the drug-contacting portion of the infusion pump.

The deformation of the plastic syringe into the desired predetermined shape and dimension serves not only to assure an accurate and predictable calibration of the drug in the syringe, but simultaneously also improves the seal between the syringe and the cooperating movable plunger, thereby preventing leakage of the drug out of the syringe barrel.

A principal additional feature of the invention is a novel construction of a gear box-type speed conversion arrangement having facilities for selecting one of N discrete, successive speed reduction settings between its input and output shafts. The gear box is so configured that each speed reduction setting is a prescribed fraction (e.g., 9/10) of the speed reduction of the next-preceeding setting. Such a configuration is ideally suited for driving the plunger of the syringe barrel of an infusion pump of the above type, since extremely fine control of the settings of the drug dose rate can be accomplished by coupling the syringe barrel plunger to the output shaft of the gear box. In addition, by coupling a constant-speed prime mover, such as a synchronous motor, to the input shaft of such gear box, the danger of inadvertent changes in the dose rate caused by changes in the line voltage applied to the motor is minimized.

Advantageously, the output shaft of the gear box is coupled to the plunger by an arrangement including a main unidirectional clutch and a pair of symmetrically disposed lead screws, which extend through corresponding threaded bores in a housing whose front end is affixed to the rear end of the plunger extending into the syringe barrel.

An additional feature of the invention is the provision of facilities for adding a one-shot increase in dosage into the fluid flow rate set by the moving plunger without interruption of the previously set flow rate. For this purpose, a knob-actuated auxiliary unidirectional clutch is associated with the main clutch that connects the output of the gear box with the input side of the twin lead screws. In particular, when the dose addition is desired, the knob is actuated rapidly to cause the auxiliary clutch to override the main clutch and to thereby incrementally advance the instantaneous angular position of the lead screws to correspondingly increment the plunger.

BRIEF DESCRIPTION OF THE DRAWING

The invention is further set forth in the following detailed description taken in conjunction with the appended drawing, in which.

DETAILED DESCRIPTION

Figure 1:
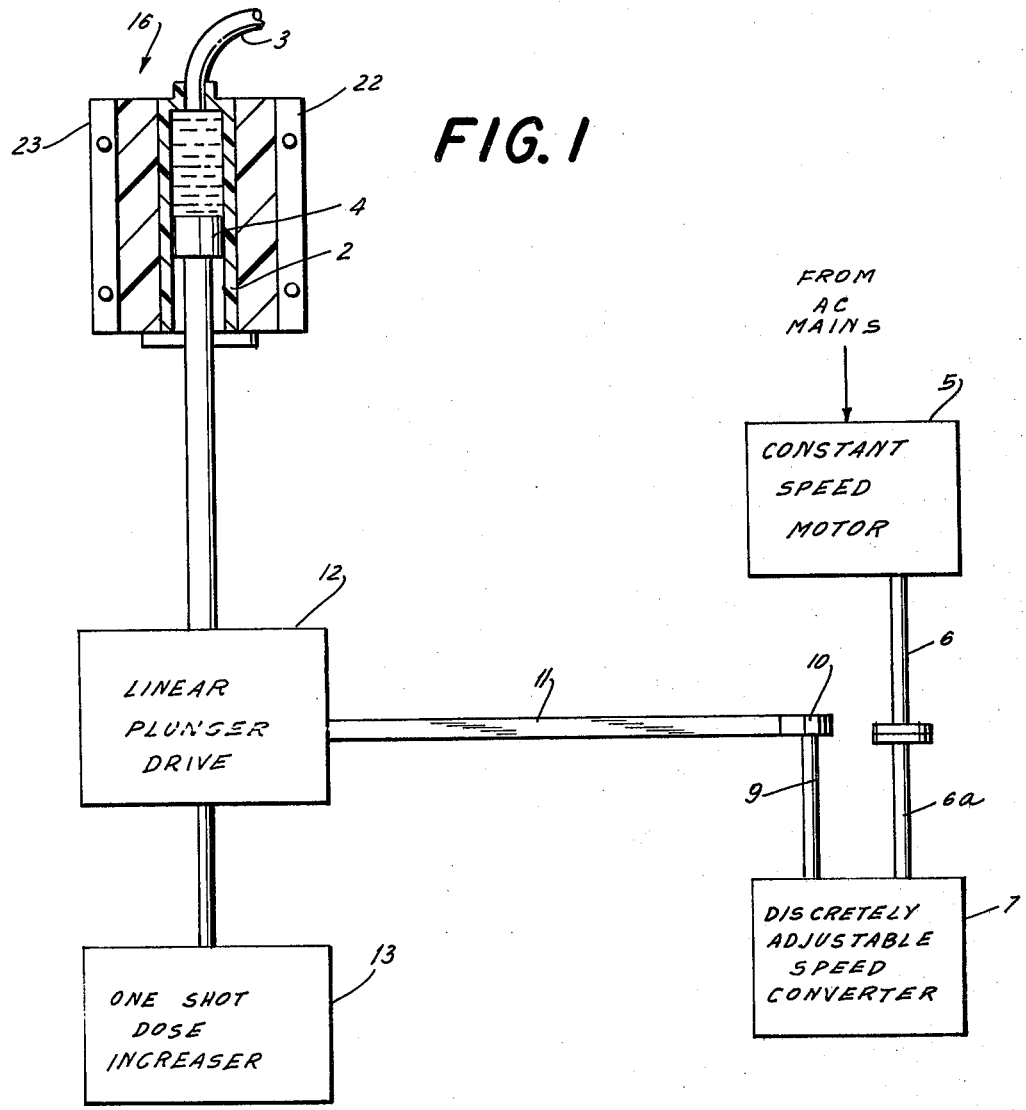
FIG. 1 is a combined block and pictorial diagram of an improved infusion pump constructed in accordance with the invention.

Referring now to the drawing, FIG. 1 illustrates one embodiment of an improved infusion pump constructed in accordance with the invention. The infusion pump includes a standard, "throw-away," thin-walled syringe barrel, represented generally at 2, which is adapted in a conventional manner to hold a quantity of medication therein for the controlled administration thereof to a patient through an outlet tubing 3, connected to a front end of the syringe.

A front end of a plunger 4, which is adapted for sliding movement within the barrel of the syringe 2, is moved forwardly therein at a selectable rate corresponding to the required rate of administration of the medication to the patient in the manner described below.

Typically, the syringe element 2 may be a pre-sterilized, 50 cc (2 ounce) plastic syringe, which is conventionally discarded after ejection of the drug from the syringe.

In order to drive the plunger at one of a plurality of pre-selected speeds corresponding to the required dose rate, the infusion pump further includes a constant speed motor 5, which may be powered from a conventional AC source. An output shaft 6 of the synchronous motor 5 is coupled to an input shaft of a discretely adjustable speed converter 7, in the form of an improved gear box arrangement described below. The converter 7 includes facilities for stepping down the constant speed of rotation of the input shaft of the converter to that of an output shaft 8 thereof by the use of one of N arbitrarily selectable, successive speed reduction settings, which are arranged so that each speed reduction setting selected is a prescribed nominal fraction of the speed reduction established by the next-preceeding setting. In practice, it has been found desirable to make each speed reduction setting equal to 90% of the next-preceeding speed reduction setting. If this is done, and if N is selected at 43, the speed range of the output shaft 9 relative to the input shaft, and thereby the range of dose rate of the drug from the syringe 2, can be selected in the range of 64:1 as indicated below.

The output shaft 9 of the converter 7 is coupled, through a toothed pulley 10 and a drive chain 11, to the input of a linear plunger drive system 12. The system 12, which may be arranged symmetrically with a pair of lead screws as described below, is adapted to linearly advance the plunger 4 within the disposable syringe 2 at a rate proportional to the rate of rotation of the output shaft 9 of the converter 7.

The plunger drive system 12 is provided with overriding facilities to permit the superposition, on the normal dose rate established by the plunger movement, of a one-shot incremental advance of the plunger, after which the plunger movement immediately reverts to the previously set dose rate. The one-shot introduction facilities, described below, are represented at 13.

In order to accurately maintain the extremely small dosage rates necessary with an infusion pump (e.g., several milliliters per hour), it is necessary that the internal dimensions of the disposable syringe 2 be as accurate as possible. Moreover, it is important that the drug stored in the barrel of the syringe 2 be inhibited from leaking out of the syringe through the space between the syringe wall and the plunger 4. Unfortunately, throw-away syringes of the type contemplated normally meet neither of these requirements, leading both to irregularities in the dose rate setting and to poor fit of the plunger inside the barrel. On the other hand, the substitution of a more accurate and more expensive glass syringe for the throw-away plastic syringe imposes extremely stringent requirements for washing and sterilizing such glass syringe after each use to prevent extreme injury to, and even death of, the next patient caused by residual contaminants in the glass syringe.

Figure 2:
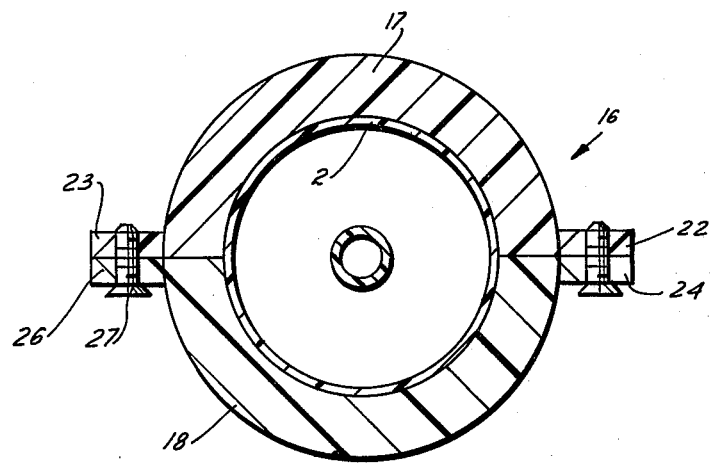
FIG. 2 is a sectional view of a composite syringe barrel portion of the arrangement of FIG. 1, employing a split cylindrical clamp illustrated in its closed position around a conventional disposable plastic syringe.
Figure 3:
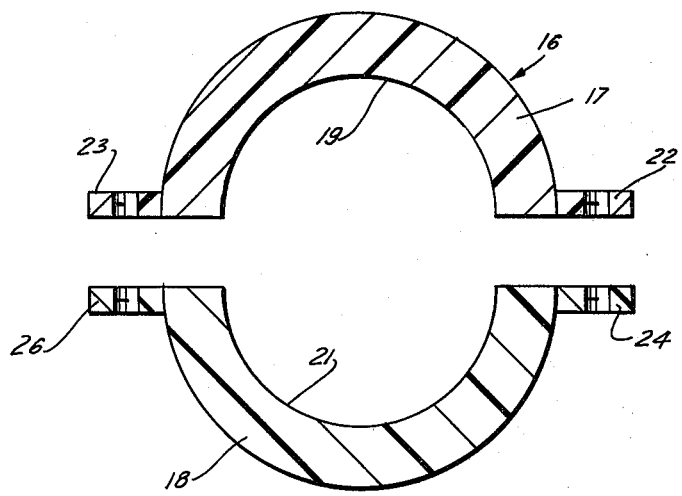
FIG. 3 is a sectional view, similar to FIG. 2, but showing the split cylindrical clamp in its open position.

In accordance with the invention, all of such problems are solved by associating, with a standard throw-away plastic syringe of the type indicated at 2, a split, thick-walled cylindrical clamp represented generally at 16 in FIGS. 2 and 3. The clamp 16 includes a pair of cooperating elongated blocks 17, 18 of a rigid plastic material, such as lucite. The block 17 is provided with a substantially semicircular recess 19, and the block 18 is provided with a corresponding semicircular recess 21. The recesses 19 and 21 cooperate, when the blocks 17 and 18 are brought into engagement in the manner indicated in FIGS. 2 and 3, to define a substantially circular opening whose diameter is slightly less than the nominal outer diameter of the wall of the disposable syringe 2.

The clamp 16 is provided with a suitable force-applying arrangement for squeezing the constituent blocks 17, 18 together to bring the semicircular recesses 19, 21 thereof into registration in the manner shown in FIG. 2. For this purpose, a pair of oppositely disposed abutment plates 22, 23 are secured to the outer periphery of the block 17. Illustratively, each of the plates 22, 23 extend completely along the length of the block 17 as shown best in FIG. 1. In like manner, a corresponding pair of abutment plates 24, 26 are secured to the outer periphery of the complementary block 18 in registration with the plates 22, 23, and with the apertures in the opposed plates 22, 24 and 23, 26 being in alignment.

The length of the constituent blocks of the clamp 16 are made coextensive with the barrel length of the disposable syringe 2. Consequently, when the syringe 2 is placed inside the clamp 16 and the blocks 17, 18 forced toward each other between the position shown in FIG. 3 and the position shown in FIG. 2, the plastic wall of the syringe 2 is deformed by the radial inward pressure resulting from this action, so that the syringe wall conforms to the accurate semicircular profile of the opening defined by the recesses 19, 21. By this means, the syringe 2 acts as a sterile plastic liner for the interior of the clamp 16, and the inner dimensions of the syringe 2 are rendered sufficiently accurate to assure a precise and repeatable dose rate to the patient.

In addition, the squeezing of the wall of the syringe 2 by the clamp 16 will be effective to decrease the leakage gap ordinarily occurring between the outer periphery of the plunger 4 and the surrounding wall of the syringe 2, thereby almost completely cutting off any undesired residual leakage.

The radial inward clamping force of the blocks 17, 18 on the surrounded syringe 2 may be successively increased by associating suitable split block clamp fasteners, illustratively a plurality of threaded bolts 27, with the aligned openings in the respective pairs of abutment plates 23, 26 and 22, 24. By employing suitable spring washers with the bolts 27, or by threading one of the two aligned apertures in the abutment plates corresponding to each of the bolts 27, a desired compressive force on the syringe 2 may be accomplished until the two halves of the clamp 16 are brought together into their closed position shown in FIG. 2. Because of the fact that the clamp 16 is axially coextensive with the barrel of the syringe 2, such radial clamping force will be uniformly applied to the syringe 2 throughout its entire length.

An additional feature of the arrangement shown in FIGS. 2 and 3 is the use of the split clamp 16 as a go-no go gauge for the inspection of the outer diameter of the syringe 2, which normally arrives from the manufacturer with an actual outer diameter larger than the nominal outer diameter. In particular, the presence of an excessively large diameter of the syringe is indicated in FIGS. 2 and 3 by the failure of the bolts 27, extending through the plates 26 and 24, to reach the opposite plates 23 and 22, respectively, to start their clamping process.

Figure 4:
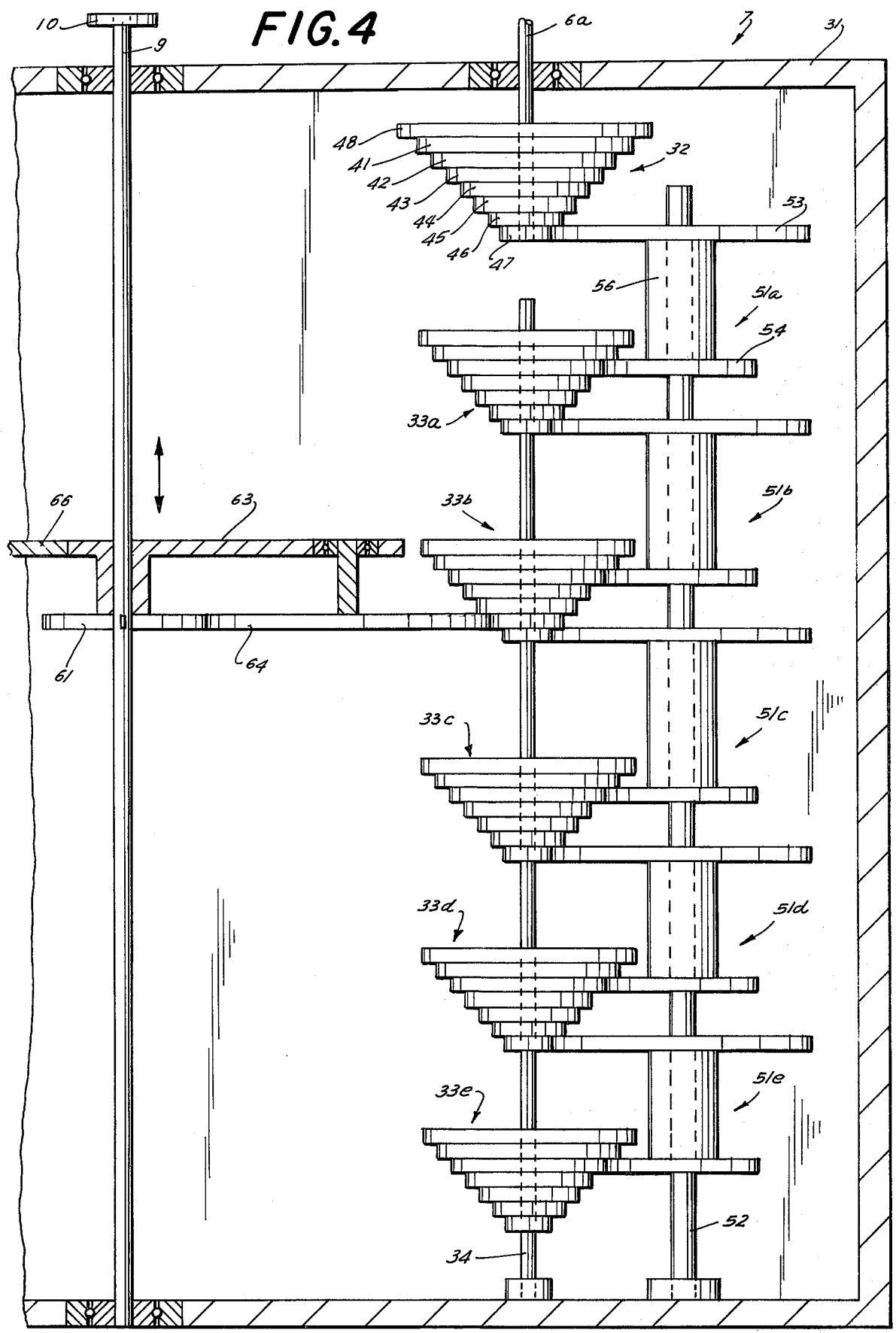
FIG. 4 is an elevation view of an improved gear box employed as a discretely adjustable speed converter in the arrangement of FIG. 1.
Figure 5:
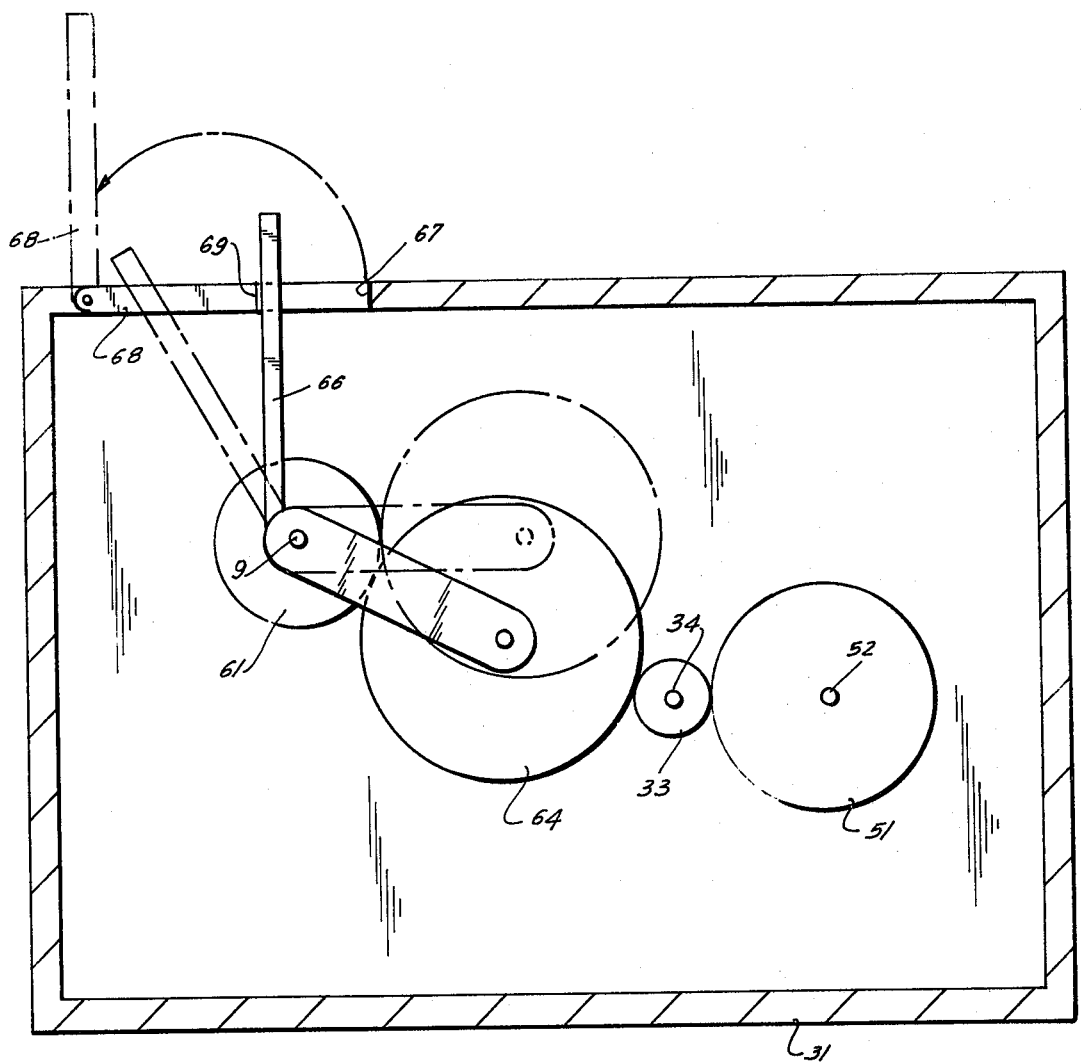
FIG. 5 is a top view of the speed converter of FIG. 4, illustrating additional facilities for the interlocking of the arrangement.

The novel gear box shown in FIGS. 4 and 5 has wide application as a flexible and efficient speed conversion device because of its capability of reducing its speed at any one of its arbitrary settings by a constant fraction to obtain the next-succeeding setting, so that the steps of speed increment provided thereby are related in a constant manner to the speed of the next-preceeding step, as well as to the speed of the input shaft. Such feature makes such gear box particularly advantageous for use as a discretely adjustable speed converter 7 in the infusion pump of FIG. 1 to vary the dose rate of the drug being administered by a constant fraction of the next-preceeding dose rate. Such feature, obviously, can be employed to yield constant percentage increments in dose rate, which are particularly necessary when extremely potent drugs are being administered. The gear box has been conveniently labeled in FIGS. 4 and 5 with the numeral 7 to indicate its applicability as the speed converter in the arrangement of FIG. 1.

Illustratively, the gear box constituting the converter 7 in FIGS. 4 and 5 includes an enclosure 31 for housing a plurality of gear clusters subdivided into a first cluster 32 and a plurality (illustratively 5) of second clusters 33a – 33e. Each of the clusters 32 and 33 includes, in the arrangement depicted, seven rigidly connected gears 41 – 47 which are disposed in longitudinally successive relation and which individually bear successively smaller numbers of teeth on their periphery. In addition, the cluster 32 has an eighth gear 48, such gear being larger than any of the remaining gears 41 – 47 and disposed in contact with the associated first gear 41 of the cluster 32 as shown.

The cluster 32 is rigidly secured to the input shaft (designated 6a) of the converter 7, which shaft is rotatably supported in the enclosure 31. The remaining clusters 33a – 33e are individually mounted for free rotation about a first auxiliary shaft 34, which is fixedly mounted in the enclosure 31 in alignment with the input shaft. The clusters 33a – 33e are longitudinally spaced at equal intervals along the shaft 34.

A plurality of gear carriers 51a – 51e, in the form of idler pairs, are individually and successively supported for rotation on a second auxiliary shaft 52, which is fixedly supported in the enclosure 31 in parallel spaced relation to the first auxiliary shaft 34 and the input shaft. Each of the carriers 51 includes an upper gear 53 and a lower gear 54 coupled to respectively opposite ends of a central abutment member 56. The gear 53 is provided with twice the number of teeth as the gear 47. The gear 54 has the same number of teeth as the gear 43. The shaft 52 is so spaced from the adjacent shaft 34 that, taking the carrier 51a as illustrative, the associated upper gear 53 is in engagement with the smallest gear 47 on the cluster 32 while the associated lower gear 54 of the carrier 51a is in engagement with the third gear 43 of the initial second cluster 33a on the shaft 34. Since the cluster 32 rotates at the speed of the input shaft, and since the cluster 33a and the carrier 51a are individually mounted for rotation on their respective shafts, the carrier 51a will be effective to provide a 2:1 speed reduction between the first cluster 32 (and thus the input shaft) and the initial second cluster 33a.

In like manner, the upper gears 53 of each of the remaining carriers 51b – 51e are individually in engagement with the smallest gears 47 of the clusters 33a – 33d, while the lower gears 54 of the clusters 51b – 51e are individually in engagement with the third gears 43 of the clusters 33b – 33e.

With such arrangement, the cluster 33b will rotate at one-half the speed of the cluster 33a; the cluster 33c will rotate at one-half the speed of the cluster 33b; and so on.

The output shaft 9 of the converter 7 is splined along its length and is supported for rotation in the enclosure 31. In order to transmit the motion of a selected one of the gears on the rotating clusters 32 and 33 to the output shaft 9, an output gear 61 is splined to the shaft 9 in such a manner that such gear 61 can be moved along the shaft 9 into transverse alignment with any of the total of 48 individual gears on the clusters 32 and 33.

The output gear 61 is supported for rotation in an abutment member 62, which is secured on its opposite end to a carrier member 63. The abutment member 62 and the carrier member 63 individually have apertures therein which are larger than the largest diameter of the splined shaft 9, so that such members may be pivoted about the shaft 9 independently of the output gear 61 rotatably supported therein. The carrier member 63 is further adapted to rotatably support an auxiliary gear 64, which is positioned in engagement with the output gear 61 and which is adapted to directly engage one of the 43 gears on the clusters 32 and 33a when the carrier member 63 is suitably pivoted toward such clusters in the manner shown in FIG. 5. The pivoting of the carrier member 63 is accomplished by means of an attached handle 66, which projects through an opening 67 in the enclosure 31 to cooperate with a spring-loaded door 68 to effect an interlock operation, the door 68 normally being biased into a position extending transversely across and closing the opening 67.

When the handle 66 is in an operative position, shown in solid lines in FIG. 5, the auxiliary gear is maintained in firm engagement with the selected one of the gears on the clusters 32 and 33, thereby to couple the motor 5 to the plunger 4 via the converter 7 and the plunger drive 12 and thereby effect a flow of medication to the patient. Conversely, when the handle is moved counterclockwise from its solid-line position to the inoperative or dotted-line position shown in FIG. 5, the auxiliary gear 64 is placed out of engagement with the clusters to stop the drug flow.

The spring-loaded door 68 extends in a not-illustrated manner along the enclosure 31 parallel to the output shaft 9, and is provided at longitudinally spaced intervals with a series of 43 staggered transverse steps, one of which is depicted in FIG. 5 and designated at 69.

The step 69 is so positioned that if for any reason the auxiliary gear 64 is not fully engaged with one of the gears on the clusters 32 and 33 (i.e., so that the handle 66 is not completely in its solid-line position shown), the step 69 will contact the handle and prevent the door from closing.

Once the door 68 is in its closed position, the step 69 serves to confine the handle 66 in its operative, solid-line position to assure continuity of the drug flow. In order for the handle to be moved counterclockwise into its inoperative position, it is necessary to first open the door 68 against the biasing force thereon.

The relative number of teeth on the common gears 41 − 47 of all of the clusters 32 and 33, and the number of teeth of the extra gear 48 on the cluster 32, are so selected, in cooperation with the 2:1 speed reduction between the clusters 32 and 33a, the clusters 33a and 33b, and so forth, that the speed of rotation of the splined output shaft 9 will be varied by successively smaller increments as the auxiliary gear 64 engages successively lower ones of the gears on the clusters shown in FIG. 4. Quantitatively, the speed of the shaft 9 when the gear 64 engages the gear 41 on the cluster 32 is selected to be about 90% of the speed of such output shaft when the gear 64 engages the upper gear 48 on the cluster 32. In like manner, the speed of the output shaft 9 when the gear 64 engages the gear 42 of the cluster 32 is selected to be about 90% of the speed of such output shaft when the gear 64 engages the next-higher gear 41; and so forth. The numerical increment in speed between successive settings, therefore, will be come finer and finer as the gear 64 proceeds downwardly along the clusters.

Table 1 below illustrates a typical set of relationships between the numbers of teeth of each of the gears on the several clusters shown in FIG. 4 and the corresponding relative rotational speed of the output shaft 9 corresponding to the engagement by the auxiliary gear 64 of each such cluster gear, with the engagement of the uppermost gear 48 corresponding to an arbitrary reference value of 128.

TABLE I

| Cluster | Gear | Number of Teeth | Relative Speed of Output Shaft | |
|---|---|---|---|---|
| 32 | 48 | 96 | 128 | (extra speed) |
|  | 41 | 87 | 116 | |
|  | 42 | 79 | 105 | |
|  | 43 | 72 | 96 | |
|  | 44 | 65 | 87 | |
|  | 45 | 59 | 79 | |
|  | 46 | 53 | 71 | |
|  | 47 | 48 | 64 | |
| 33a | 41 | 87 | 58 | |
|  | 42 | 79 | 53 | |
|  | 43 | 72 | 48 | |
|  | 44 | 65 | 43 | |
|  | 45 | 59 | 39 | |
|  | 46 | 53 | 35 | |
|  | 47 | 48 | 32 | |
| 33b | 41 | 87 | 29 | |
|  | 42 | 79 | 26 | |
|  | 43 | 72 | 24 | |
|  | 44 | 65 | 22 | |
|  | 45 | 59 | 20 | |
|  | 46 | 53 | 18 | |
|  | 47 | 48 | 16 | |
| 33c | 41 | 87 | 14.5 | |

TABLE I-continued

| Cluster | Gear | Number of Teeth | Relative Speed of Output Shaft |
|---|---|---|---|
|  | 42 | 79 | 13 |
|  | 43 | 72 | 12 |
|  | 44 | 65 | 11 |
|  | 45 | 59 | 10 |
|  | 46 | 53 | 9 |
|  | 47 | 48 | 8 |
| 33d | 41 | 87 | 7.3 |
|  | 42 | 79 | 6.6 |
|  | 43 | 72 | 6.0 |
|  | 44 | 65 | 5.4 |
|  | 45 | 59 | 4.9 |
|  | 46 | 53 | 4.4 |
|  | 47 | 48 | 4.0 |
| 33e | 41 | 87 | 3.6 |
|  | 42 | 79 | 3.3 |
|  | 43 | 72 | 3.0 |
|  | 44 | 65 | 2.7 |
|  | 45 | 59 | 2.46 |
|  | 46 | 53 | 2.2 |
|  | 47 | 48 | 2.0 |

As clearly evident from Table 1, an overall speed change of 64:1 is obtainable with the 43 settings of the gear box shown in FIG. 4, with the increments between the speeds established by the last cluster 33e being significantly smaller than the increments established by the gears on the cluster 32.

Figure 6:
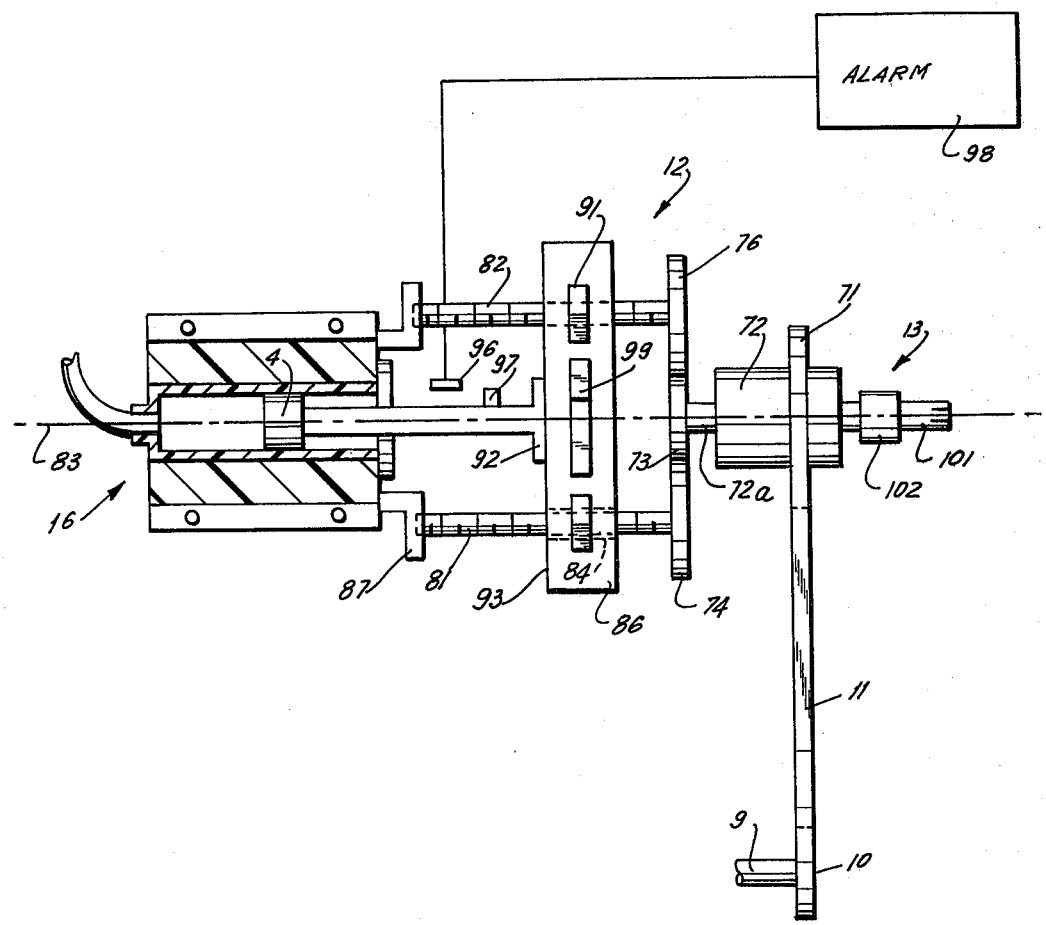
FIG. 6 is a longitudinal view of a twin-lead screw embodiment of the linear plunger drive of FIG. 1, illustrating additional facilities for the introduction of a one-shot increase in dosage from the infusion pump.

One embodiment of the linear plunger drive 12 of FIG. 1 is shown in FIG. 6. The pulley 10 affixed to the output shaft 9 of the speed converter 7 is coupled, via the drive chain 11, to a pulley 71 of a unidirectional clutch 72. The output shaft (designated 72a) of the clutch 72 is affixed to a gear 73, which engages a pair of gears 74 and 76 on radially opposite sides thereof.

A pair of lead screws 81, 82 having angular screw threads thereon are individually affixed at their rear ends to the gears 74, 76.

The lead screws 81, 82 extend parallel to a longitudinal axis 83 of the plunger. The respective lead screws 81, 82 project through an associated pair of bores 84 disposed in a housing 86, and are individually supported for rotation at their front ends within an abutment member 87 which, in turn, may be secured to the rear end of the split cylindrical clamp 16.

A pair of split threaded housings 91 are individually supported within the bores 84 to serve as nuts which are selectively drivingly engageable with the lead screws 81, 82 extending therethrough. The nuts 91 are normally yieldably loaded into their closed position in engagement with the respective lead screws, so that the rotation of the gears 74, 76 by the drive chain 11 through the split clutch 72 will cause the housing 86 to advance along the longitudinal axis 83 of the plunger 4. In order to move the plunger 4 in synchronism with the housing 86, a rear end 92 of the plunger is suitably secured to a front surface 93 of the housing 86.

With the above arrangement, it will be noted that the plunger 4 will be moved forwardly within the syringe 2 in a precise and controlled manner at a linear speed proportional to the selected output speed of the gear box output shaft 9, with the precision of such linear movement being guaranteed by the completely symmetric lead-screw drive depicted in FIG. 6. In the event of jamming or binding of the plunger, the triangular threads of the lead screws will exert respective wedging actions against the nuts 91 to open the nuts and thereby prevent a further advancing force on the plunger.

In order to warn an attendant when the amount of medication remaining within the syringe 2 has decreased below an acceptable minimum, a limit switch 96 may be positioned adjacent the path of travel of the plunger between the housing 86 and the abutment member 87, with a cooperating actuating element 97 serving to close the microswitch and actuate an audible alarm 98. The alarm is actuated when the housing has reached a point of travel along its forward path corresponding to the point of an unacceptably low residual amount of the drug.

In order to quickly and conveniently return the plunger to its rear-most position for insertion into the next syringe 2 to be used in the apparatus, a lever 99 is carried in the housing 86 for cooperation with the spring-loaded nuts 91. In particular, a manual actuation of the lever 99 when the housing has reached its front-most position will cause the spring-loaded nuts 91 to open. At this point, the housing 86, and thereby the attached plunger 4, can be moved back and forth freely.

The one-shot dosage adjustment means 13 of FIG. 1 is embodied, in the arrangement of FIG. 6, as an external knob 101 coupled to the shaft 72a of the clutch 72 through a second unidirectional clutch 102. Thus, the shaft 72a is driven either by clutch 72 or by clutch 102, whichever is moving faster at any particular instant. The knob 101 and the clutch 102 cooperate with the clutch 72 so that a rapid manual rotation of the knob 101 while the clutch 72 is being driven at its normal very slow speed by the drive chain 11 will cause the shaft 72a, and thereby the gear 73, to be incrementally rotated forwardly by a degree proportional to the amount of rotation of the knob 101, thereby superimposing a corresponding angular increment to each of the lead screws 81 and 82 via the gears 74 and 76 coupled to the gear 73. Such incremental advance will be accomplished without disturbing the previously set dose rate of the infusion pump established by the speed of the converter output shaft 9. The corresponding additional dosage may be manually added by rotation of the knob 101 at any time that is deemed necessary during the continuous infusion.

In the foregoing, an illustrative arrangement of the invention has been described. Many variations and modifications will now occur to those skilled in the art. It is accordingly desired that the scope of the appended claims not be limited to the specific disclosure herein contained.

What is claimed is:

1. In an infusion pump for delivering a metered amount of a drug, cylindrical barrel means adapted to receive a quantity of the drug, the barrel means having an open rear end for receiving the front end of a plunger and further having an opening in a forward wall thereof through which the drug can be ejected upon a forward movement of the plunger in the barrel means, the barrel means comprising, in combination, a thin-walled, relatively compliant cylindrical syringe adapted to receive the plunger and having a nominal outer diameter, a cylindrical clamping member axially coextensive with and radially positionable coaxially over the syringe, the inner diameter of the clamping member being adjustable inwardly to an inner limit representing a fixed standard inner diameter smaller than the nominal outer diameter of the syringe, and means for releasably applying an inwardly directed radial clamping force to the clamping member to deform the wall of the syringe into conformance with the standard inner diameter of the clamping member, whereby the syringe forms an intimately adhering liner for the clamping member.

2. An infusion pump as defined in claim 1, in which the clamping member comprises a pair of thick-walled blocks, the blocks respectively having confronting arcuate surfaces cooperable to define a syringe-receiving opening of the standard inner diameter.

3. An infusion pump as defined in claim 2, in which the blocks are formed from a rigid plastic material.

4. An infusion pump as defined in claim 3, in which the rigid plastic material is lucite.

5. An infusion pump as defined in claim 1, further comprising means coupled to the rear end of the plunger for sliding the plunger forwardly in the syringe at an adjustable rate, the rate of movement of the plunger determining the instantaneous rate of ejection of the drug.

6. An infusion pump as defined in claim 5, in which the plunger sliding means comprises, in combination, adjustable speed conversion means having a first input shaft and a second output shaft, means coupled between the first and second shafts for establishing one of N successive speed reduction settings therebetween, the establishing means being arranged so that the speed of the second shaft at each speed reduction setting is a prescribed nominal fraction of its speed at the next-preceeding setting, a constant-speed motor, means for coupling the motor to the first shaft, and output means for normally coupling the second shaft to the rear end of the plunger.

7. An infusion pump as defined in claim 6, in which the nominal fraction is 90%.

8. An infusion pump as defined in claim 6, in which the establishing means comprises, in combination, a plurality of gear clusters, each cluster having a plurality of gears fixedly disposed in successive, axially spaced concentric relation, the successive gears in each cluster having progressively smaller numbers of teeth, means for fixedly mounting a first one of the clusters to the first shaft, a third shaft, means for independently and successively mounting each of the remaining clusters for rotation on the third shaft in axially spaced relation, first speed-reducing means for coupling the first cluster to an initial one of the remaining clusters in the succession on the third shaft, a plurality of second speed-reducing means for coupling each of the remaining clusters on the third shaft to the next-succeeding one of the clusters on the third shaft, and input-output ratio selection means carried on the second shaft for engaging an arbitrary gear of any of the clusters on the first and third shafts.

9. An infusion pump as defined in claim 8, in which the first and third shafts are disposed in axially aligned relation, in which the second shaft is supported in parallel spaced relation to the aligned first and third shafts opposite the gear clusters thereon, and in which the ratio selection means comprises, in combination, a carrier member mounting for sliding movement on and pivotal movement about the second shaft toward and away from the aligned first and third shafts, and gear means associated with the carrier member for engagement with the arbitrary one of the cluster gears.

10. An infusion pump as defined in claim 9, in which the speed conversion means further comprises, in combination, an enclosure surrounding the clusters on the aligned first and third shafts and the carrier member on the second shaft, the enclosure having therein an access opening bounded between first and second opposed walls, an operating handle connected to the carrier member for pivoting the carrier member about the second shaft between a first position in which the associated gear means are in engagement with one of the gears on the clusters and a second position in which the gear means are out of engagement with the clusters, the handle means extending outwardly through the access opening and toward the first wall of the opening when in the first position, a spring-loaded door pivotally mounted to the enclosure and biased for movement across the access opening into a closed position, and means disposed on the door means and operable when the door moves toward its closed position for engaging the handle means to prevent the door from closing unless the handle means is in its first position.

11. An infusion pump as defined in claim 8, in which the first speed-reducing means comprises means for imparting an angular speed reduction of 2:1 from the first cluster to the initial cluster on the third shaft, and in which each second speed-reducing comprises means for imparting an angular speed reduction of 2:1 between the associated clusters.

12. An infusion pump as defined in claim 6, in which the output coupling means comprises, in combination, a first support surface fixedly associated with the clamping member, a movable housing having at least one bore extending therethrough and disposed axially behind the first support surface, threaded nut means axially carried in the housing bore, at least one lead screw extending through the nut means in the bore of the housing for driving cooperation with the nut means, means for rotatably connecting a front end of the lead screw to the first support surface whereby a rotation of the lead screw effects a forward axial advance of the housing toward the first support surface from a rear position of the housing, means for securing a rear end of the plunger to a front end of the housing, and means for drivingly connecting the second shaft to a rear end of the lead screw for rotating the lead screw in timed relation to the rotation of the second shaft.

13. An infusion pump as defined in claim 6, in which the output coupling means comprises, in combination, a first support surface associated with the clamping member, a movable housing having a pair of bores extending axially therethrough on symmetrically opposite side of a central axis thereof, a pair of threaded nut means coaxially carried in the respective bores, a pair of lead screws individually extending through the nut means in the respective bores for driving cooperation with the associated nut means, means for rotatably connecting a front end of each of the lead screws to the first support surface whereby a simultaneous rotation of the lead screws will effect a forward axial advance of the housing toward the first support surface from a rear position of the housing, means for securing a rear end of the plunger to a front end of the housing along the axis thereof, and means for symmetrically connecting the second shaft to the respective rear ends of the lead screws for rotating the lead screws in timed relation to the rotation of the second shaft.

14. An infusion pump as defined in claim 12, in which the lead screw has an angular screw thread, and in which the threaded nut means comprises a split nut housing normally biased into a closed position in engagement with the lead screw, and in which the infusion pump further comprises externally operable lever means disposed on the housing for selectively operating the split nut housing away from its closed position.

15. An infusion pump as defined in claim 5, further comprising means associated with the plunger sliding means for superimposing, on the plunger movement determined by the plunger sliding means, a forward movement increment of predetermined amplitude.

16. An infusion pump as defined in claim 12, in which the engaging means comprises, in combination, an auxiliary shaft, means for coupling the rear end of the lead screw to the auxiliary shaft, and means for coupling the second shaft to the auxiliary shaft.

17. An infusion pump as defined in claim 16, in which the means for coupling the second shaft to the auxiliary shaft includes first unidirectional clutch means; and in which the pump further comprises, in combination, externally actuable second unidirectional clutch means coupled to the auxiliary shaft and adapted to override the first clutch when the instantaneous speed of rotation of the second clutch means is greater than that of the first clutch means for incrementally advancing the instantaneous angular position of the auxiliary shaft.

18. An infusion pump as defined in claim 12, further comprising alarm means coupled to the housing for generating an output indication when the housing has moved forwardly from its rear position by a predetermined increment.

* * * * *